(12) United States Patent
Marzouk et al.

(10) Patent No.: US 9,402,790 B2
(45) Date of Patent: Aug. 2, 2016

(54) LIQUID LAUNDRY DETERGENTS WITH PERFUME CAPSULES

(71) Applicant: Henkel AG & Co. KGaA, Duesseldorf (DE)

(72) Inventors: Ashraf Marzouk, Cairo (EG); Ulrich Pegelow, Duesseldorf (DE); Annika Gueldner, Duesseldorf (DE); Simone Nemmertz, Erkrath (DE); Thorsten Ott, Moenchengladbach (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/031,177

(22) Filed: Sep. 19, 2013

(65) Prior Publication Data
US 2014/0017307 A1    Jan. 16, 2014

Related U.S. Application Data

(63) Continuation of application No. PCT/EP2012/054477, filed on Mar. 14, 2012.

(30) Foreign Application Priority Data

Mar. 22, 2011  (EP) .................... 11159249

(51) Int. Cl.
| | |
|---|---|
| A61K 8/04 | (2006.01) |
| C11D 1/83 | (2006.01) |
| C11D 3/37 | (2006.01) |
| C11D 3/50 | (2006.01) |
| C11D 10/04 | (2006.01) |
| C11D 17/00 | (2006.01) |
| C11D 1/22 | (2006.01) |
| C11D 1/29 | (2006.01) |

(52) U.S. Cl.
CPC . *A61K 8/044* (2013.01); *C11D 1/83* (2013.01); *C11D 3/3765* (2013.01); *C11D 3/505* (2013.01); *C11D 10/045* (2013.01); *C11D 17/003* (2013.01); *C11D 17/0013* (2013.01); *C11D 17/0026* (2013.01); *C11D 17/0039* (2013.01); *C11D 1/22* (2013.01); *C11D 1/29* (2013.01)

(58) Field of Classification Search
USPC .......................... 435/183; 252/186.1, 186.42
See application file for complete search history.

(56) References Cited

U.S. PATENT DOCUMENTS

| | | | |
|---|---|---|---|
| 6,339,058 B1 | 1/2002 | Toussaint et al. | |
| 6,362,156 B1 * | 3/2002 | Hsu et al. | 510/418 |
| 6,380,150 B1 * | 4/2002 | Toussaint et al. | 510/425 |

FOREIGN PATENT DOCUMENTS

| | | | | |
|---|---|---|---|---|
| EP | 0385534 | * | 9/1990 | .......... D06M 13/467 |
| WO | 2010/048154 A2 | | 4/2010 | |
| WO | WO2010/048154 | * | 4/2010 | .............. A61P 17/16 |

OTHER PUBLICATIONS

Horiba Scientific (A Guidebook to Particle Size Analysis pp. 1-29, 2012).*
Frankia Symbiosis (Proceedings of the 12th International Meeting on Frankia and Actinorhizal Plants; Kluwer Academic Publishers, 2003, p. 71 col. 2 paragraph 1).*
PCT International Search Report (PCT/EP2012/054477) dated Jul. 18, 2012.

* cited by examiner

*Primary Examiner* — Anna Falkowitz
(74) *Attorney, Agent, or Firm* — Thomas G. Krivulka

(57) ABSTRACT

The present invention relates to a structured liquid composition comprising anionic surfactant, nonionic surfactant and a plurality of stable and evenly suspended encapsulated actives. The liquid composition is externally structured by incorporating a cross-linked acrylic copolymer.

7 Claims, No Drawings

LIQUID LAUNDRY DETERGENTS WITH PERFUME CAPSULES

FIELD OF THE INVENTION

The present invention generally relates to a structured liquid composition comprising anionic surfactant, nonionic surfactant and a plurality of encapsulated actives. The present invention also describes a method for manufacturing such a liquid composition.

BACKGROUND OF THE INVENTION

Liquid detergents comprising microcapsules are very appealing to consumers. The inclusion of microcapsules in liquid detergents is desirable not only for aesthetic reasons but also for functional reasons such as isolation of incompatible ingredients, controlled and/or delayed release, etc. Ideally, the microcapsules are stably suspended in the liquid detergent and only dissolve/disintegrate in-use.

Since consumers generally desire a clean and fresh odor whenever they open the package and smell the product, as well as at later points in their laundering experience such as a clean and fresh odor in the laundry room, and on laundered clothing, perfume microcapsules have been used in consumer products to improve fragrance deposition, retention and longevity.

One problem encountered with the production of liquid detergents comprising encapsulated actives is that the distribution of the encapsulated actives within the liquid matrix needs to be controlled so that the encapsulated actives do not overly float, sink or otherwise gravitate during processing, when packaged for later processing with other ingredients, or when in a packaged consumer product. In order to properly disperse and suspend the encapsulated actives with the liquid matrix, structuring agents can be introduced into the composition. There are number of compounds which can provide structuring benefits.

Known external structuring agents include polymers or gums such as gellan gum, alginate, carrageenan, xanthan gum, and guar gum. Although gums have been used to provide structuring benefits, the gums have been found to be undesirable due to any pH and electrolyte level sensitivity which can decrease their structuring capacity or lead to other undesirable issues such as composition opacity or gelling or clumping of product.

As disclosed in WO2010/048154 A2 bacterial celluloses or non-polymeric crystalline hydroxyl-functional materials also provide structuring benefits.

A drawback of many external structurants is their need for special processing conditions. In addition, many external structurants have to be used in high amounts in order to provide the desired structuring effect.

It is an object of the present invention to provide a liquid detergent comprising encapsulated actives, wherein the encapsulated actives are stably suspended and wherein the liquid detergent can be manufactured in an easy and cheap way.

This object is achieved by a structured liquid composition comprising:
(a) anionic surfactant at a level of from 10% up to 25% by weight of said composition, said anionic surfactant comprising linear alkylbenzene sulphonate and fatty alcohol ether sulfate;
(b) nonionic surfactant at a level of from 5% up to 15% by weight of said composition,
(c) a structurant at a level of from 0.1% to 2% by weight of said composition, said structurant comprising a cross-linked acrylic copolymer;
(d) a plurality of encapsulated actives at a level of from 0.05% up to 0.22% by weight of said composition, wherein the encapsulated actives have a $d_{90}$ value of below 20 μm.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A structured liquid composition comprising: anionic surfactant at a level of from 10% up to 25% by weight of said composition, said anionic surfactant comprising linear alkylbenzene sulphonate and fatty alcohol ether sulfate; nonionic surfactant at a level of from 5% up to 15% by weight of said composition, a structurant at a level of from 0.1% to 2% by weight of said composition, said structurant comprising a cross-linked acrylic copolymer; a plurality of encapsulated actives at a level of from 0.05% up to 0.22% by weight of said composition, wherein the encapsulated actives have an $d_{90}$ value of below 20 μm.

A method for manufacturing a structured liquid composition comprising: anionic surfactant at a level of from 10% up to 25% by weight of said composition, said anionic surfactant comprising linear alkylbenzene sulphonate and fatty alcohol ether sulfate; nonionic surfactant at a level of from 5% up to 15% by weight of said composition; a structurant at a level of from 0.1% to 2% by weight of said composition, said structurant comprising a cross-linked acrylic copolymer; a plurality of encapsulated actives at a level of from 0.05% up to 0.22% by weight of said composition, wherein the encapsulated actives have an $d_{90}$ value of below 20 μm, wherein the structurant is added in the form of an o/w emulsion.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly been found that the use of a cross-linked acrylic copolymer in combination with a selected anionic/nonionic surfactant system leads to a structured liquid composition in which encapsulated actives can be stably suspended with a minimum amount of structurant.

It is preferred that the anionic surfactant is present at a level of from 15% up to 25% by weight of said composition and, preferably, at a level of from 20% up to 25% by weight of said composition.

Anionic surfactants are important ingredients of laundry detergents because of their cleansing and emulsifying properties. Anionic surfactants are particularly good at keeping the dirt away from fabrics, and removing oily soil residues from fabrics. It has surprisingly found that anionic surfactants can be used in high amounts without being detrimental to the structuring capacity of the structurant.

Furthermore, it is preferred that the anionic surfactant additionally comprises a fatty acid soap. The structured liquid composition according to the present invention even tolerates additional amounts of fatty acid soap.

In another preferred embodiment of the invention the structurant is a cross-linked acrylic copolymer comprising methacrylic acid and ethyl acrylate as monomers. Acrylic copolymer structurants comprising methacrylic acid monomers and ethyl acrylate monomers provide excellent structuring capacity and need only be added in low amounts. Accordingly, it is preferred that the structurant is present at a level of from 0.15% up to 1% by weight of the liquid composition and, even more preferred, at a level of from 0.2% up to 0.6% by weight of the liquid composition.

In a yet another preferred embodiment of the invention encapsulated actives have a $d_{90}$ value of below 15 µm and, more preferred, a $d_{90}$ value of below 10 µm.

It is preferred that encapsulated active comprises a friable microcapsule, a moisture-activated microcapsule, a heat-activated microcapsule, or combinations thereof.

Depending on the use and the purpose of the encapsulated active different types of encapsulation techniques are used. The liquid structured composition is able to stably suspend these different types of microcapsules.

It is preferred that the encapsulated active comprises an active selected from the group consisting of perfumes, softening agents, anti-static agents, refreshing agents, anti-microbial agents, disinfecting agents, anti-wrinkle agents, malodor control agents, insect/pet repellents, skin/fabric conditioning agents, silicones, anti-microbials, brighteners, bleaches, antifoams, and combinations thereof. In a more preferred embodiment of the invention the encapsulated active comprises a perfume as an active.

Due to the physical or chemical characteristics of actives, actives may be incompatible with other compositional components of the liquid composition or may be lost during post application processes such as rinsing or drying. By encapsulating actives their stability, delivery and release can be improved and controlled. Since a clean and fresh odor of the laundry composition and/or on laundered clothing is very important for consumers, by encapsulating perfumes an improved perfume delivery at all stages can be achieved.

The invention also relates to a method for manufacturing a structured liquid composition comprising:
(a) anionic surfactant at a level of from 10% up to 25% by weight of said composition, said anionic surfactant comprising linear alkylbenzene sulphonate and fatty alcohol ether sulfate;
(b) nonionic surfactant at a level of from 5% up to 15% by weight of said composition,
(c) a structurant at a level of from 0.1% to 2% by weight of said composition, said structurant comprising a cross-linked acrylic copolymer; a plurality of encapsulated actives at a level of from 0.05% up to 0.22% by weight of said composition, wherein the encapsulated actives have an $d_{90}$ value of below 20 µm,
wherein the structurant is added in the form of an o/w emulsion.

By using a cross-linked acrylic copolymer as structurant no special processing conditions such as activation of the structurant by applying mechanical forces or pre-swelling. Consequently, the liquid composition can be obtained at low costs.

The invention is described in greater detail below on the basis of examples, among other things.

In general, the present invention relates to a structured liquid composition comprising a specified anionic surfactant mixture at a specified level, nonionic surfactant, a cross-linked acrylic copolymer structurant, and a plurality of encapsulated actives, wherein the encapsulated actives have an $d_{90}$ value of below 20 µm.

The liquid composition comprises anionic surfactant at a level of from 10% up to 25% by weight of said composition, preferably, at a level of from 15% up to 25% by weight of said composition and, and even more preferred, at a level of from 20% up to 25% by weight of said composition.

The anionic surfactant comprises linear alkylbenzene sulphonate and fatty alcohol ether sulfate.

Fatty alcohol ether sulfates are water-soluble salts of the formula $RO(A)_m SO_3M$, in which R is an unsubstituted $C_{10}$-$C_{24}$-alkyl or -hydroxyalkyl radical, preferably a $C_{12}$-$C_{20}$-alkyl or -hydroxyalkyl radical, more preferably $C_{12}$-$C_{18}$-alkyl or -hydroxyalkyl radical. A is an ethylene oxide or propylene oxide unit, m is an integer greater than 0, preferably between approximately 0.5 and approximately 6, more preferably between approximately 0.5 and approximately 4, and M is a cation, for example sodium, potassium, lithium, calcium, magnesium, ammonium or a substituted ammonium cation. Specific examples of substituted ammonium cations are methyl-, dimethyl-, trimethylammonium and quaternary ammonium cations such as tetramethylammonium and dimethylpiperidinium cations, and also those which are derived from alkylamines such as ethylamine, diethylamine, triethylamine or mixtures thereof. Preferred examples include $C_{12}$-$C_{18}$ fatty alcohol ether sulfates where A is an ethylene oxide unit and the content of ethylene oxide units is 1, 2, 2.5, 3 or 4 mol per mole of the fatty alcohol ether sulfate, and in which M is sodium or potassium. Fatty alcohols with 1 to 4 ethylene oxide units, in particular 1 to 2 ethylene oxide units. A particularly preferred fatty alcohol ether sulfate is sodium lauryl ether sulfate with 2 ethylene oxide units.

The amount of fatty alcohol ether sulfate is preferably from 1 to 10% by weight of said composition and more preferably from 2 to 9% by weight of said composition.

The linear alkylbenzene sulphonate is preferably a linear alkylbenzene sulphonate having an alkyl chain length of $C_8$-$C_{15}$. In particular, the linear alkylbenzene sulphonate is a $C_9$-$C_{13}$ alkyl benzene sulphonate, a $C_{10}$-$C_{13}$ alkyl benzene sulphonate or a $C_{10}$-$C_{15}$ alkyl benzene sulphonate.

The amount of linear alkylbenzene sulphonate is preferably from 3 to 20% by weight of said composition, more preferably from 5 to 18% by weight of said composition and especially from 7 to 15% by weight of said composition.

Further anionic surfactants that may additionally be present in the liquid structured composition are fatty acid soaps. Saturated and unsaturated fatty acid soaps, such as the salts of lauric acid, myristic acid, palmitic acid, stearic acid, (hydrogenated) erucic acid, and behenic acid, are suitable, as are soap mixtures derived in particular from natural fatty acids, e.g. coconut, palm-kernel, olive-oil, or tallow fatty acids.

The amount of fatty acid soap is preferably from 1 to 8% by weight of said composition, more preferably from 2,5 to 7% by weight of said composition and especially from 4 to 6% by weight of said composition.

The anionic surfactants, including the fatty acid soaps, can be present in the form of their sodium, potassium, or ammonium salts and as soluble salts of organic bases such as mono-, di-, or triethanolamine. The anionic surfactants are preferably present in the form of their sodium or potassium salts, in particular in the form of the sodium salts.

It is preferred that the liquid composition only contains fatty alcohol ether sulfates, linear alkylbenzene sulphonates and fatty acid soaps as anionic detergents.

The liquid composition comprises a nonionic surfactant at a level of from 5% up to 15% by weight of the liquid composition.

The nonionic surfactants used are by preference alkoxylated, advantageously ethoxylated, in particular primary alcohols having by preference 8 to 18 carbon atoms and an average of 1 to 12 mol ethylene oxide (EO) per mol of alcohol, in which the alcohol residue can be linear or preferably methyl-branched in the 2-position, or can contain mixed linear and methyl-branched residues, such as those that are usually present in oxo alcohol residues. Particularly preferred, however, are alcohol ethoxylates having linear residues made up of alcohols of natural origin having 12 to 18 carbon atoms, e.g. from coconut, palm, tallow, or oleyl alcohol, and an average of 2 to 8 EO per mol of alcohol. The preferred ethoxylated alcohols include, for example, $C_{12-14}$ alcohols with 3 EO, 4 EO, 5 EO, or 7 EO, $C_{9-11}$ alcohols with 7 EU, $C_{13-15}$ alcohols with 3 EO, 5 EO, 7 EO, or 8 EO, $C_{12-18}$ alcohols with 3 EO, 5 EU, or 7 EO, and mixtures thereof, such as mixtures of $C_{12-14}$ alcohol with 3 EO and $C_{12-18}$ alcohol with 7 EO. The degrees of ethoxylation indicated represent statistical averages, which can correspond to an integral or a fractional number for a specific product. Preferred alcohol ethoxylates exhibit a restricted distribution of homologs (narrow range ethoxylates, NRE). In addition to these nonionic surfactants, fatty alcohols with more than 12 EO can also be used. Examples of these are tallow fatty alcohol with 14 EO, 25 EO, 30 EO, or 40 EO. Nonionic surfactants that contain EO and PO groups together in the molecule are also usable according to the present invention. Block copolymers having EO-PO block units or PO-EO block units, but also EO-PO-EO copolymers or PO-EO-PO copolymers, can be used in this context. Also usable, of course, are mixed alkoxylated nonionic surfactants in which EU and PO units are distributed statistically rather than in block fashion. Such products are obtainable by the simultaneous action of ethylene oxide and propylene oxide on fatty alcohols. These nonionic surfactants are obtainable, for example, under the commercial name Dehydol® (from Cognis).

Also suitable nonionic surfactants are mixtures of a (more) branched ethoxylated fatty alcohol and a non-branched ethoxylated fatty alcohol, such as mixtures of $C_{16-18}$ fatty alcohol having 7 EO and 2-propylheptanol having 7 EO.

Further classes of nonionic surfactants used in preferred fashion are alkoxylated fatty acid alkyl esters, surfactants of the amine oxide type, polyhydroxy fatty acid amides or alkylpolyglucosides.

Most preferred the liquid composition comprises a $C_{12-18}$ fatty alcohol having 7 EO or a $C_{13-15}$ oxo alcohol having 7 EO as nonionic surfactant.

It is essential for the present invention that the liquid composition comprises a cross-linked acrylic copolymer as structurant. The structurant is present at a level of from 0.1% to 2% by weight of the liquid composition. In a preferred embodiment the structurant is present at a level of from 0.15% up to 1% by weight of the liquid composition and, in an even more preferred embodiment the structurants is present at a level of from 0.2% up to 0.6% by weight of said composition.

Preferably the structurant is an anionic acrylic copolymer. It is preferred that the structurant is a cross-linked acrylic copolymer comprising methacrylic acid and ethyl acrylate as monomers. It is also preferred that the acrylic copolymer is not hydrophobically modified which means that the acrylic copolymer does not contain a monomer bearing an alkyl or an aryl group having eight or more carbon atoms. Suitable cross-linked acrylic copolymers comprising methacrylic acid and ethyl acrylate as monomers are Polygel W 400 or Synthalen W 400 available from 3V Sigma.

After dissolving in water a copolymer comprising methacrylic acid and ethyl acrylate as monomers forms a network structure that is especially suited to stabilize and suspend small capsules, especially capsules having a $d_{90}$ value of below 20 µm.

It may be preferred that the liquid composition comprises a combination of two or more structurants with the proviso that the further structurant is not a gum. But it is more preferred that the liquid composition comprises the cross-linked acrylic copolymer as sole structurant.

The cross-linked acrylic copolymer is preferably used in the form of an o/w emulsion and, thus, can be added during any step of the production process of the liquid composition.

The liquid composition comprises a plurality of encapsulated actives at a level of from 0.05% up to 0.22% by weight of the liquid composition. It is preferred that the encapsulated active comprises an active selected from the group consisting of perfumes, softening agents, anti-static agents, refreshing agents, anti-microbial agents, disinfecting agents, anti-wrinkle agents, malodor control agents, insect/pet repellents, skin/fabric conditioning agents, silicones, anti-microbials, brighteners, bleaches, antifoams, and combinations thereof. In one embodiment the encapsulated active comprises a perfume as an active.

The encapsulated actives have a $d_{90}$ value of below 20 µm, preferably a $d_{90}$ value of below 15 µm, more preferred a $d_{90}$ value of below 10 µm and most preferred a $d_{90}$ value of below 5 µm.

The $d_{90}$ defines that equivalent diameter where 90 mass-% of the encapsulated actives have a smaller diameter.

It is preferred that the encapsulated active comprises a friable microcapsule, a moisture-activated microcapsule, a heat-activated microcapsule, or combinations thereof.

The encapsulated active preferably comprises a friable microcapsule. "Friability" refers to the propensity of the microcapsules to rupture or break open when subjected to direct external pressures or shear forces. For purposes of the present invention, the microcapsules utilized are "friable" if, while attached to fabrics treated therewith, they can be ruptured by the forces encountered when the capsule-containing fabrics are manipulated by being worn or handled (thereby releasing the contents of the capsule).

Although a preferred embodiment of the present invention is directed to actives encapsulated within friable microcapsules, the present invention is not being limited to only those microcapsules.

Typically, microcapsules comprise a spherical hollow shell of water insoluble or at least partially water insoluble material, typically polymer material, within which the active is contained.

Useful shell materials include materials selected from the group consisting of polyethylenes, polyamides, polystyrenes, polyisoprenes, polycarbonates, polyesters, polyacrylates, polyureas, polyurethanes, polyolefins, polysaccharides, epoxy resins, vinyl polymers, and mixtures thereof. Suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In a preferred embodiment, the shell material comprises melamine cross-linked with formaldehyde.

Microcapsules may be prepared using a range of conventional methods known to those skilled in the art for making shell capsules, such as interfacial polymerization, and polycondensation. With the help of these methods a thin polymer shell is created around droplets or particles of an active emulsified or dispersed in a carrier liquid.

Usually, the encapsulated active is introduced into the liquid composition in the form of an aqueous slurry of the microcapsules.

In a preferred embodiment, the active comprises a perfume. Non-limiting examples of suitable perfumes include blooming perfumes, perfume oils, and perfume raw materials comprising alcohols, ketones, aldehydes, esters, ethers, nitriles alkenes, and mixtures thereof.

In another preferred embodiment, the liquid composition comprises an encapsulated perfume and a free perfume.

A general range of encapsulated active concentration, for example perfume microcapsules content, of the microcapsules slurry is between 1 and 50%, by weight, relative to the weight of the slurry, the latter also containing typically 4 to 20% by weight of encapsulating shell material in a free form, and the balance being water.

Preferably, the liquid composition is a liquid washing or cleaning composition. More preferred the liquid composition is an aqueous washing or cleaning composition and most preferred the liquid composition is an aqueous laundry washing or cleaning composition.

In addition to the surfactant mixture of anionic surfactant and nonionic surfactant, the structurant, and the plurality of encapsulated actives, a liquid washing or cleaning composition may contain further ingredients that further improve the applications-engineering or aesthetic properties of the washing or cleaning agent. In the context of the present invention, the washing or cleaning agent by preference additionally contains one or more substances from the group of the detergency builders, bleaching agents, bleach activators, bleach catalysts, enzymes, non-aqueous solvents, pH adjusting agents, free perfumes, fluorescing agents, dyes, hydrotopes, silicone oils, anti-redeposition agents, anti-gray agents, shrinkage preventers, wrinkle protection agents, dye transfer inhibitors, antimicrobial active substances, germicides, fungicides, antioxidants, preservatives, corrosion inhibitors, antistatic agents, bittering agents, ironing adjuvants, proofing and impregnation agents, swelling and anti-slip agents, softening compounds, complexing agents and UV absorbers.

From the above mentioned further ingredients detergency builders, enzymes, non-aqueous solvents, pH adjusting agents, free perfumes, fluorescing agents, dyes, silicone oils, soil-release polymers, anti-gray agents, dye transfer inhibitors, and preservatives are most preferred included into a liquid washing or cleaning composition.

The liquid composition, in particular the liquid washing or cleaning composition, according to the present invention can be used to wash and/or clean textile fabrics.

The liquid composition is manufactured using usual and known methods and processes. For example, the constituents of the liquid composition can be simply mixed in agitator vessels, the water, non-aqueous solvent, and surfactants usefully being prepared first. The fatty acid component, if present, is then saponified at 50 to 60° C. The further constituents, including the structurant, preferably in the form of an o/w emulsion, are then added in portions. In a final stage, the encapsulated active is added and evenly distributed within the liquid composition.

Table 1 below shows the composition of one liquid composition E1 according to the present invention, and of four comparative examples V1 to V4. Quantities are indicated in wt % of active matter.

TABLE 1

|  | E1 | V1 | V2 | V3 | V4 |
|---|---|---|---|---|---|
| $C_{11\text{-}13}$-alkylbenzenesulfonic acid, Na salt | 7 | 7 | 7 | 7 | 7 |
| Sodium lauryl ether sulfate with 2 EO | 9 | 9 | 9 | 9 | 9 |
| $C_{12\text{-}18}$ fatty alcohol with 7 EO | 7 | 7 | 7 | 7 | 7 |
| Coconut fatty acid, | 5.6 | 5.6 | 5.6 | 5.6 | 5.6 |
| Cross-linked acrylic copolymer* | 0.5 | — | 0.5 | 0.5 | — |
| Acrylic copolymer (not cross-linked)** | — | — | — | — | 1 |
| Xanthan gum | — | — | 0.25 | — | — |
| Xanthan gum/guar gum (1:1) | — | 1 | — | — | — |
| Perfume microcapsules ($d_{90}$ = 15 µm) | 0.2 | 0.2 | 0.25 | — | 0.2 |
| Perfume microcapsules ($d_{90}$ = 25 µm) | — | — | — | 0.2 | — |
| Silicone foam suppressant | 0.01 | 0.01 | 0.01 | 0.01 | 0.01 |
| Phosphonic acid | 0.2 | 0.2 | 0.2 | 0.2 | 0.2 |
| Fluorescent dye | 0.05 | 0.05 | 0.05 | 0.05 | 0.05 |
| Enzymes, dyes, preservatives | + | + | + | + | + |
| Water | To make 100 | | | | |

*Polygel W 400 (purchased from 3V Sigma)
**Acusol ® 820 (purchased from Rohm & Haas; copolymer of methacrylic acid, ethylacrylate and stearyl oxypolyethylmethacrylic having approximately 20 moles of ethylene oxide)

Only liquid composition E1 according to the present invention gives rise to a stable liquid composition in which the perfume microcapsules are evenly and stably suspended. The comparative liquid compositions V1 to V4 showed creaming or settling out of the perfume capsules already within one day.

In contrast, liquid composition E1 was even stable at 50° C. for at least 7 days.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. A structured liquid composition comprising:
   (a) anionic surfactant at a level of from 10% up to 25% by weight of said composition, said anionic surfactant comprising linear alkylbenzene sulphonate and fatty alcohol ether sulfate;
   (b) nonionic surfactant at a level of from 5% up to 15% by weight of said composition,
   (c) a structurant at a level of from 0.1% to 2% by weight of said composition, wherein said structurant is selected from the group of structurants consisting of crosslinked anionic acrylic copolymer;
   (d) a plurality of encapsulated actives at a level of from 0.05% up to 0.22% by weight of said composition, wherein the encapsulated actives have an $d_{90}$ value of below 20 µm, the encapsulated actives comprising a hollow shell within which the active is contained, wherein the shell comprises materials selected from the group consisting of reaction products of one more amines with one or more aldehydes;

(e) fatty acid soap at a level of from 2.5 to 7% by weight of said composition; and wherein the encapsulates remain stably suspended at 50° C. for at least 7 days.

2. The structured liquid composition according to claim 1, wherein said anionic surfactant is present at a level of from 15% up to 25% by weight of said composition.

3. The structured liquid composition according to claim 1, wherein said structurant is a cross-linked acrylic copolymer comprising methacrylic acid and ethyl acrylate as monomers.

4. The structured liquid composition according to claim 1, wherein said structurant is present at a level of from 0.15% up to 1% by weight of said composition.

5. The structured liquid composition according to claim 1, wherein said encapsulated active comprises a friable microcapsule, a moisture-activated microcapsule, a heat-activated microcapsule, or combinations thereof.

6. The structured liquid composition according to claim 1, wherein said encapsulated active comprises an active selected from the group consisting of perfumes, softening agents, anti-static agents, refreshing agents, anti-microbial agents, disinfecting agents, anti-wrinkle agents, malodor control agents, insect/pet repellents, skin/fabric conditioning agents, silicones, anti-microbials, brighteners, bleaches, antifoams, and combinations thereof.

7. The structured liquid composition according to claim 6, wherein said encapsulated active comprises a perfume as an active.

\* \* \* \* \*